United States Patent [19]
Murphy et al.

[11] Patent Number: 5,795,404
[45] Date of Patent: Aug. 18, 1998

[54] METHOD AND APPARATUS FOR CLEANING CHANNELS OF AN ENDOSCOPE

[75] Inventors: Kelley Murphy; Michael Lynch, both of Skaneateles; Scott Spanfelner, Camillus, all of N.Y.

[73] Assignee: Welch Allyn, Inc., Skaneateles Falls, N.Y.

[21] Appl. No.: 699,510

[22] Filed: Aug. 23, 1996

Related U.S. Application Data

[60] Provisional application No. 60/005,415 Oct. 13, 1995.
[51] Int. Cl.$^6$ .................. B08B 3/04; B08B 9/00
[52] U.S. Cl. ............ 134/22.12; 134/21; 134/22.18; 134/24; 134/34; 422/33
[58] Field of Search .................. 134/22.12, 21, 134/24, 18, 102.2, 169 C, 95.1, 166 R, 171, 22.18, 34; 422/28, 33

[56] References Cited

U.S. PATENT DOCUMENTS

| | | | |
|---|---|---|---|
| 4,281,674 | 8/1981 | Tanaka et al. | 134/95 |
| 4,288,882 | 9/1981 | Takeuchi | 15/88 |
| 4,525,220 | 6/1985 | Sasa et al. | 134/21 |
| 4,526,622 | 7/1985 | Takamura et al. | 134/21 |
| 4,526,623 | 7/1985 | Ishii et al. | 134/21 |
| 4,576,650 | 3/1986 | Yabe et al. | 134/22.12 |
| 4,579,597 | 4/1986 | Sasa et al. | 134/21 |
| 4,579,598 | 4/1986 | Sasa et al. | 134/22.12 |
| 4,637,378 | 1/1987 | Sasa | 128/4 |
| 4,667,691 | 5/1987 | Sasa | 134/169 C |
| 5,240,675 | 8/1993 | Wilk et al. | 422/22 |
| 5,494,530 | 2/1996 | Graf | 134/18 |
| 5,511,568 | 4/1996 | Bowman et al. | 134/102.2 |

*Primary Examiner*—Harold Y. Pyon
*Attorney, Agent, or Firm*—Wall Marjama & Bilinski

[57] ABSTRACT

Method and apparatus for cleaning the internal channels of a medical endoscope wherein the water bottle is replaced with a cleaning bottle adapted to pass fluids stored in the bottle into both the air and the water channels of the instrument. An end cap having a fluid reservoir is placed over the distal end of the instrument. The air/water pump and the suction pump are then cycled to pass a cleaning solution stored in the replacement bottle through the air and water channels into the end cap. The solution in the end cap is drawn through the suction line and collected in a container for disposal. The procedure is repeated using a rinse solution. The pumps are allowed to run after the rinse solution is exhausted, thus air drying the channels.

11 Claims, 4 Drawing Sheets

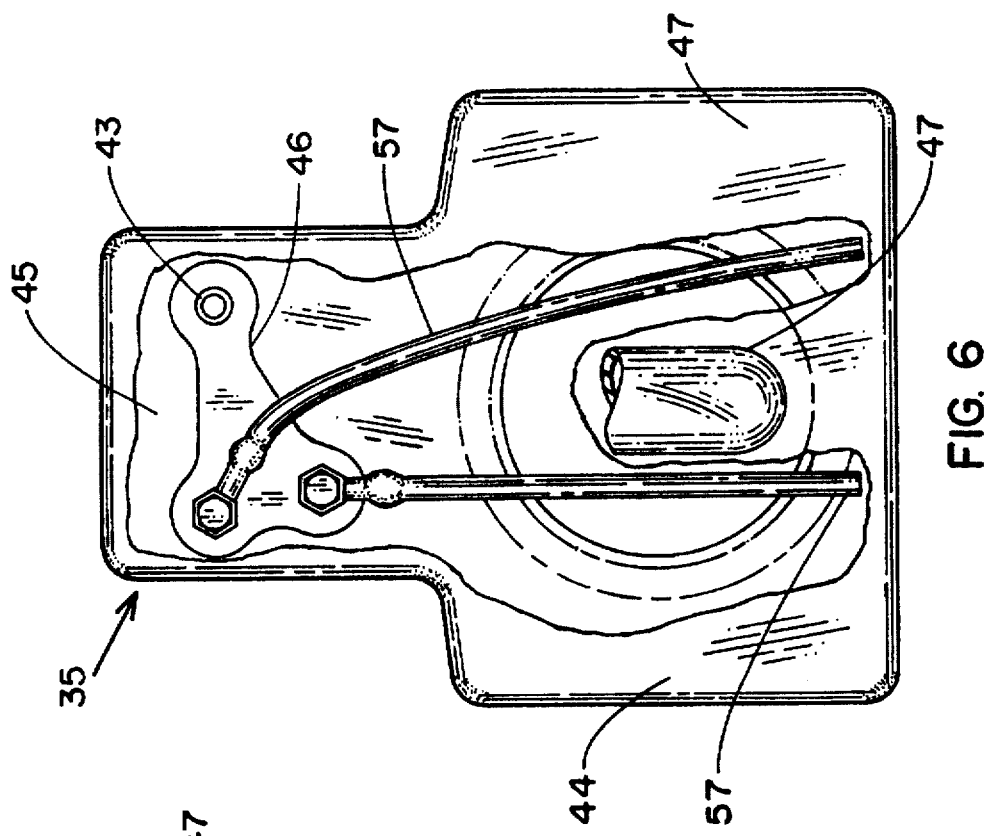
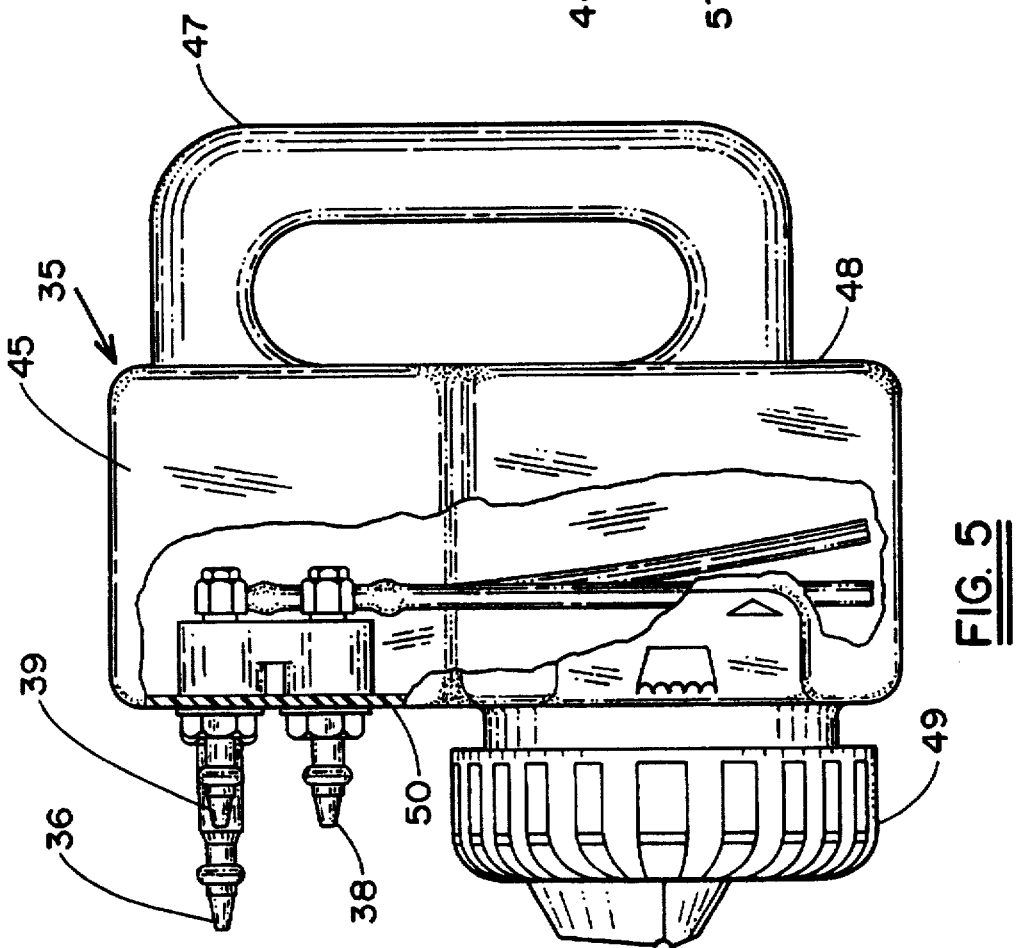

METHOD AND APPARATUS FOR CLEANING CHANNELS OF AN ENDOSCOPE

BACKGROUND OF THE INVENTION

This invention relates to endoscopic instruments and, in particular, to cleaning the interior channels of a medical endoscope after the instrument has been used to examine a patent.

Typically, medical endoscopes, such as those used to examine the gastrointestinal tract, urinary tract, and the like, contain three interior channels that pass throughout the insertion tube of the instrument from its proximal end to its distal or viewing end. These include a suction channel for removing gases and fluids from the target region being examined, a water and air channel for introducing water into the target region to either cleanse the target region or to wash the viewing optics of the instrument and an air channel is provided for introducing air into the target region to inflate the area being examined and to dry the viewing optics. The suction channel also serves as a means for introducing an exploratory instrument such as a biopsy instrument or electrosurgical instrument into the target region. To this end, a "cold" biopsy port is typically mounted on the control handle of the endoscope through which the exploratory instrument can be inserted into and passed through the suction channel.

After the endoscope has been employed in a procedure it must be thoroughly cleaned, disinfected, and sterilized before it can be reused on another patient. Prior to disinfecting and sterilizing the instrument, the interior channels must be flushed with a cleaning solution, rinsed and then dried to remove organic debris and other microbes containing contaminants from the channels.

Heretofore, cleaning of the endoscope channels was a hand operation wherein cleaning solution, rinse water, and air were injected through each of the individual channels using syringes and the like. This procedure was not only difficult to carry out, but was also time consuming thus extending the turn around time for the instrument between procedures.

SUMMARY OF THE INVENTION

It is therefore an object of the present invention to improve medical endoscopes.

It is a still further object of the present invention to improve the method of cleaning a medical endoscope between exploratory, diagnostic or therapeutic procedures.

Another object of the present invention is to reduce the amount of time required to turn around a medical instrument between procedures.

Yet another object of the present invention is to provide an automated and repeatable method of cleaning the internal channels of an endoscope.

Still another object of the present invention is to utilize the component parts of an endoscopic system to remove organic debris from the channels of a medical endoscope.

These and other objects of the present invention are attained in a medical endoscope having a proximal end and a distal end that is suitable for insertion into a body cavity. The endoscope contains a biopsy/suction channel, an air channel, and a water channel that pass through the interior of the instrument between the proximal and the distal end thereof. An end cap containing a hollow reservoir is placed upon the distal end of the instrument so that the reservoir is in fluid flow communication with the distal end of the three channels. A syringe containing a cleaning solution is mounted in the biopsy port of the instrument. The proximal end of the suction line is connected to the suction pump servicing the system while the proximal ends of the air and water lines are connected to a cleaning bottle that replaces the normal water bottle used during normal medical procedures. The cleaning bottle is specially designed to deliver the fluid contained in the bottle into both the air and the water channels of the instrument when the air water pump is activated.

Initially, the cleaning bottle is filled to a desired level with a cleaning solution, the air/water and suction valves are removed and their open wells capped. At this time the distal end of the insertion tube is capped and a syringe filled with cleaning solution is attached to the biopsy port. Both the suction pump and the air/water pump that normally serve the system are activated. Cleaning solution from the cleaning bottle is passed through the air and water channels and is delivered into the reservoir of the end cap. Under the influence of the suction pump, fluid collected in the end cap reservoir is drawn through the suction line and deposited in a container for disposal. The solution that has been loaded into the syringe is inserted in the biopsy port of the instrument and the solution is automatically drawn from the syringe by the suction pump to cleanse the biopsy port region.

The above noted procedure is repeated using a rinse. As the rinse cycle is completed, the syringe is removed and the pump is allowed to run until the channels are dry. The channels are then brushed and the endoscope disinfected using conventional soaking procedures.

BRIEF DESCRIPTION OF THE DRAWINGS

For a better understanding of these and other objects of the present invention, reference will be made herein to the following detailed description of the invention which is to be read in conjunction with the following drawings, wherein:

FIG. 4 is an end view showing the distal end of the present endoscope;

FIG. 5 is an enlarged side view showing a cleaning bottle used during a procedure carried out in accordance with the teachings of the present invention;

FIG. 6 is an enlarged back view showing the cleaning bottle illustrated in FIG. 5, and FIG. 7 is an enlarged view in section showing an end cap for covering the distal end of an endoscope.

DESCRIPTION OF THE INVENTION

Figure 1:
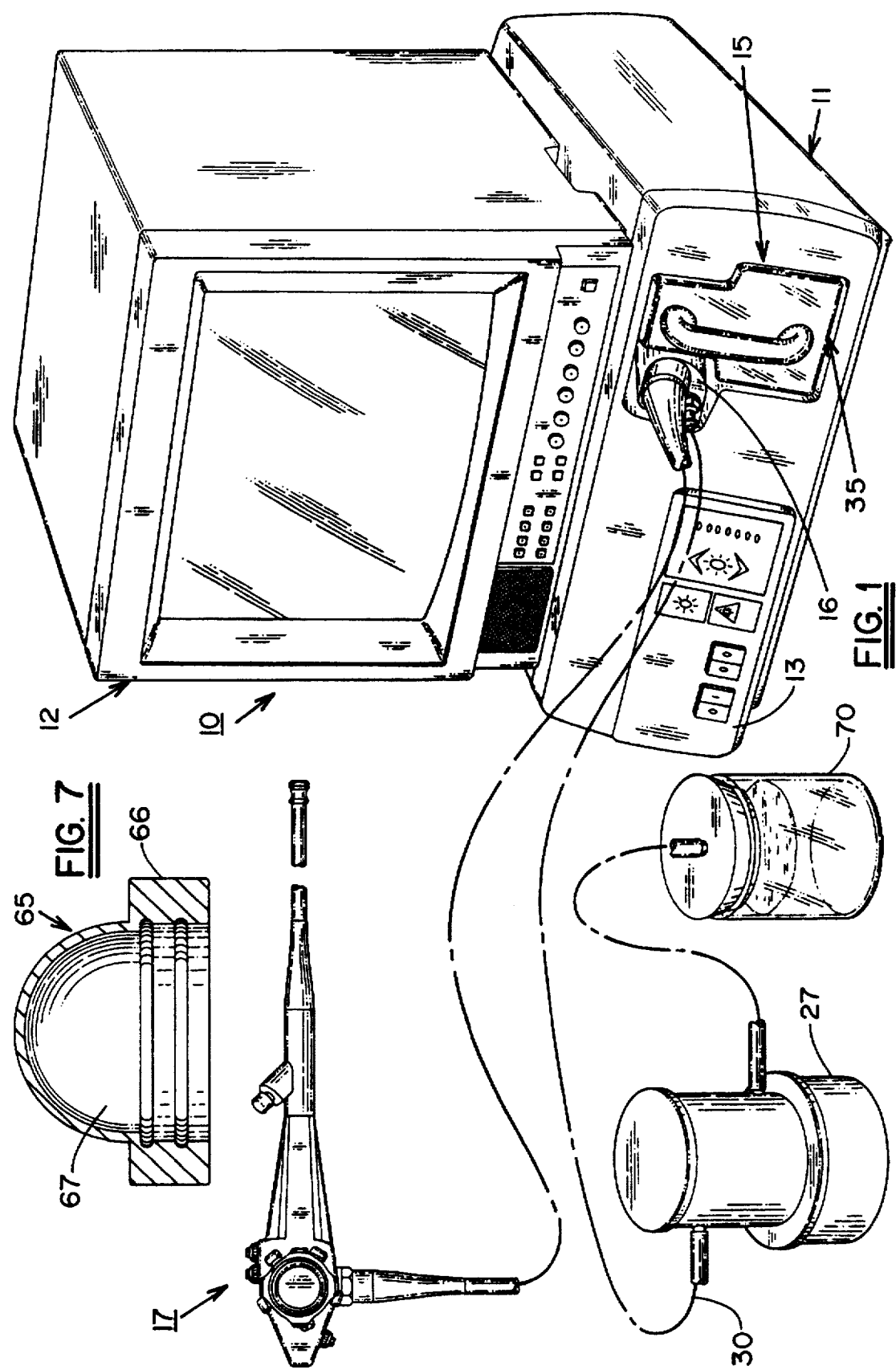
FIG. 1 is a perspective view of a video system embodying the present invention.

Turning initially to FIG. 1, there is shown a video endoscopic system, generally referenced 10, that embodies the teachings of the present invention. The system includes a light source unit 11 and a video display 12. The front face 13 of the support unit containing a plurality of controls by which various related functions can be selected and a recessed endoscope connector port 15. The connector port is adapted to receive therein an endoscope connector terminal 16 attached to the proximal end of a flexible endoscope, generally referenced 17. The endoscope as illustrated, is a flexible endoscope typically used for medical purposes for examining difficult to reach body cavities. Although the present invention will be described with reference to a video endoscope, the teachings set forth below is broad enough to also encompass fiberscopes.

As is well known in the art, an endoscope used for medical purposes must be detached from the light source and thoroughly cleaned and disinfected between procedures to prevent cross contamination between patients. As part of the cleansing procedure, the internal channels of the endoscope must be thoroughly washed with a cleaning solution, rinsed and dried prior to disinfecting the instrument to insure that all microbial carrying organic debris and other contaminants are removed from the exposed surfaces of the endoscope. As noted above, the procedures involved in cleaning the channels heretofore had to be completed by hand and were thus time-consuming and difficult to achieve. As will become evident from the disclosure below, the present invention provides an automated process for cleaning the interior channels of a medical endoscope utilizing readily available components embodied in the endoscopic system. Tests conducted on endoscopes utilizing the present cleaning procedure have shown it to be 99.99% effective in removing organic debris from the interior channels of an endoscope that had been used to examine the gastrointestinal tract of a patient.

Figure 2:
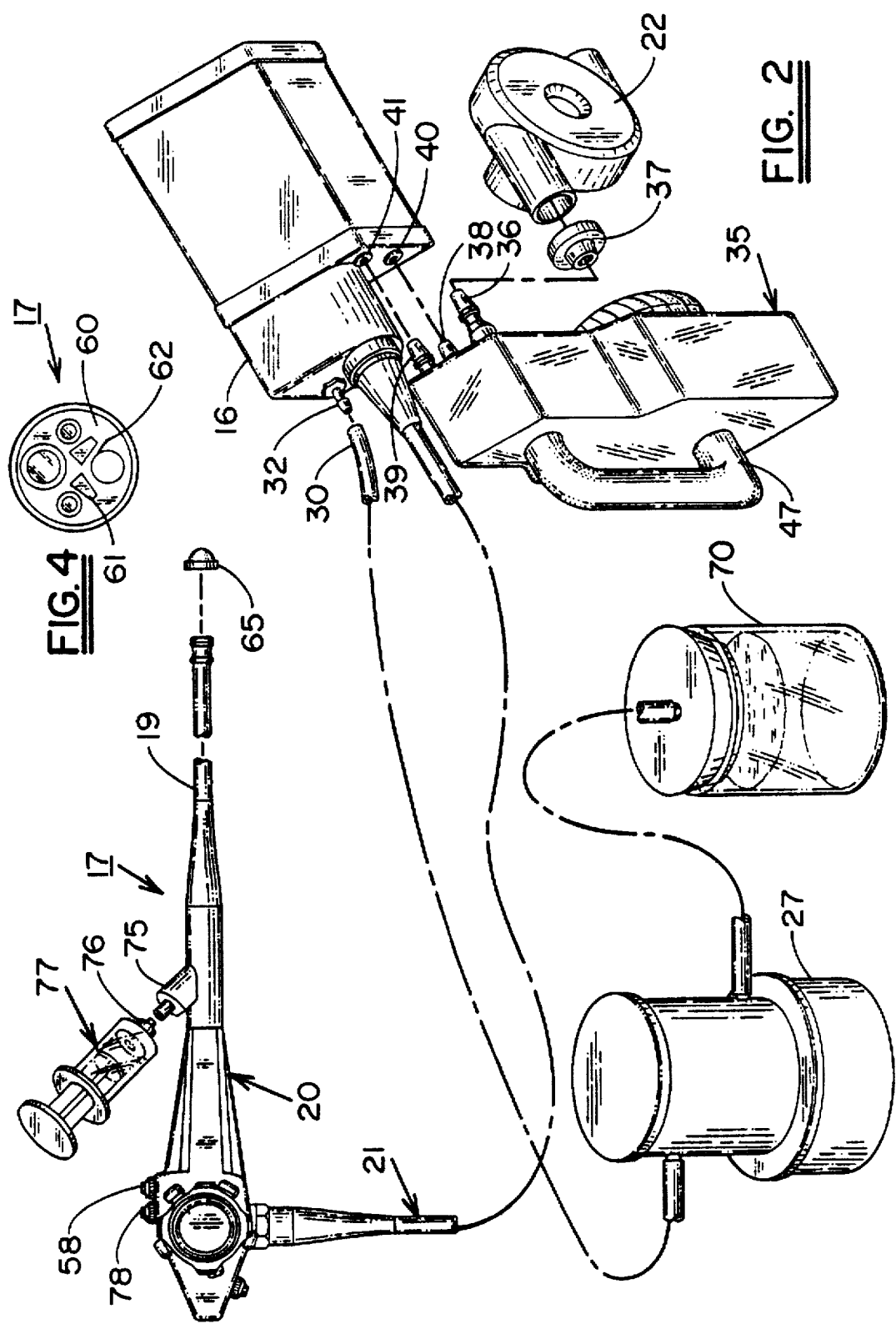
FIG. 2 is an enlarged perspective view illustrating the endoscope and cleaning bottle employed in the video system of FIG. 1.
Figure 3:
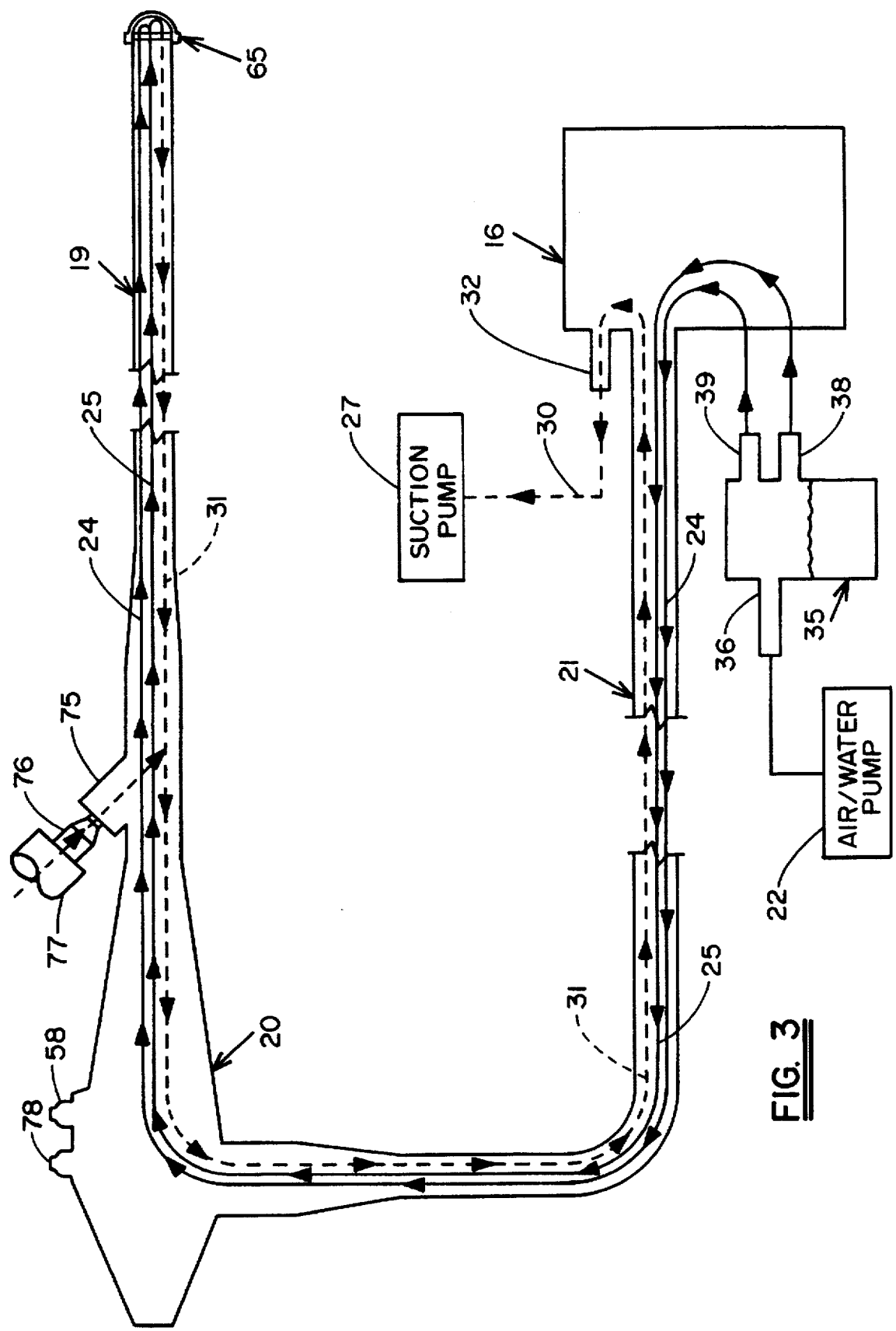
FIG. 3 is a schematic diagram of the endoscope of FIG. 2 further illustrating the flow path of a cleaning solution that is passed through the endoscope during a cleaning procedure following the teachings of the present invention.

With further reference to FIGS. 2 and 3, the endoscope 17 is of typical construction and includes an insertion tube 19, a control handle 20 and an umbilical tube 21 that is connected to an endoscope connector terminal 16. The endoscopic connector terminal 16 is adapted to be removably received within the endoscope connector port 15 (Fig. 1) which is located within the light source 11 (FIG. 1). An air/water pump 22 (FIG. 3) is also contained within the light source and, as will be explained below, communicates with the air channel 24 and the water channel 25 of the endoscope. An external suction pump 27 (FIG. 1) is further connected to a suction port 32 mounted upon the front face of the endoscope connector terminal 16. An internal connection within the module places the suction line 30 in fluid flow communication with the suction channel 31 of the endoscope.

The endoscope connector terminal 16 is further adapted to receive a cleaning bottle 35 that is substituted for a water bottle of similar construction that is normally plugged into the light source 11. The cleaning bottle has a male air connector 36 that is adapted to plug into a female pump coupling 37 attached to an air/water pump 22 stored in the light source 11. The bottle further contains a male water outlet connector 38 and a male air outlet connector 39 which, in turn, are received in the air and water couplers 40 and 41, respectively, mounted on the face of the endoscope connector terminal 16. Flow lines inside the terminal 1 (not shown) connect the air and water outlet connectors on the bottle to the air and water channels contained within the endoscope when the cleaning bottle 35 and the module 16 are plugged into endoscope connector port 15.

As illustrated in FIGS. 5, 6 and 7, the cleaning bottle 35 is formed of a suitable transparent plastic and includes a lower fluid supply chamber 44 and a smaller upper air chamber 45. A manifold 46 is mounted in the air chamber to which is connected the air and water outlet connectors 38 and 39. The air inlet connector 36 which is operatively coupled to the air/water pump 22 (FIG. 2), is coupled to an air outlet port 43 attached to the manifold. The bottle includes a handle 47 mounted upon its outer face 48 and a removable filler cap 49 mounted upon its inner face 50.

In operation the lower supply chamber 44 is filled with a solution to a desired level indicated by a level line scribed on the side of the bottle whereby an air space is created above the fluid level in the air chamber 45. The replacement bottle is then plugged into the front face of the light source, air from the air/water pump is delivered upon demand into the air chamber via an air inlet port 43 located in the manifold. The air outlet and the water outlet connectors 38 and 39 are each attached to dip tubes 57–57 that extends downwardly so that the free ends of the tubes are adjacent to the bottom wall of the bottle. Accordingly, air pressure that builds up in the air chamber forces the cleaning solution stored in the supply chamber upwardly through the dip tubes into both the air and the water channels of the endoscope.

Normally, a water bottle is plugged into the system which has a water chamber for holding a quantity of water and an air chamber over the water chamber. The water chamber is connected directly into the water channel of the instrument and the air chamber is connected directly into the air channel of the instrument. In operation, the air/water pump delivers air into the air chamber and a control valve 58 on the control handle of the instrument is selectively positioned to open and close the air and water channels and thus deliver either air or water through the distal tip of the instrument into the body region under investigation. As noted above, the replacement bottle used in the practice of the present invention contains a pair of dip tubes 57–57 that are arranged to deliver solution that is contained in the lower fluid chamber of the replacement bottle into both the air and the water channels. In a sense the dip tube's short circuit the direct air path between the air/water pump and the air channel provided by the conventional water bottle. Air can thus only enter the channel when the solution in the cleaning bottle is exhausted.

A flow reversing end cap 65 is fitted over the distal end of the insertion tube. The end cap, as illustrated in FIG. 7 is preferably formed of a deformable rubber and includes an annular flange 66 and an interior reservoir 67. The flange is arranged to pass over the distal end of the insertion tube to create a fluid tight seal therebetween. Cleaning solution discharged from the distal end of the insertion tube is collected within the reservoir 67.

To clean the channels, a replacement cleaning bottle is inserted into the light source, the air/water and suction valves are removed and their wells are capped, and both the suction pump and the air/water pump are actuated in a normal manner. Accordingly, cleaning solution is passed through the air and water channels into the end cap reservoir. The solution delivered in the end cap is drawn out of the reservoir 67 by the suction pump 27 and collected in waste container 70 (FIG. 1) for disposal.

A biopsy port 75 is situated on the control handle of the instrument through which exploratory devices can be inserted through the suction channel into the viewing region of the instrument to carry out one of many available procedures. During the cleaning procedure, a syringe 77 loaded with cleaning solution is coupled to the biopsy port entrance. The syringe is equipped with a locking mechanism 76 that forms a fluid tight seal with the port when the syringe is inserted therein. Under the influence of the suction pump the cleaning solution in the syringe is automatically drawn through the biopsy port to cleanse difficult to reach regions in the endoscope.

After the cleaning fluid has been passed through the three channels, the cleaning solution bottle is filled with a rinse solution, which can be water, and the above described procedure is repeated to rinse the previously cleansed channels. The pumps are kept activated after the rinse fluid has been depleted thus allowing air to be drawn through the channels to promote drying. After the drying operation has been completed, the channels are brushed to remove any residue that might be left behind. The suction valve 78 and the air water valve 58 on the control handle 20 are covered with suitable caps. The endoscope is then unplugged from the service unit and placed in a disinfectant bath for a required amount of time needed to disinfect the instrument.

As should be evident from the disclosure above, the present method of cleaning the channels of an endoscope is fully automated and employs the readily available system pumps to move cleansing, rinsing and drying fluids through the channels. All that is required is the way of additional hardware is a modified replacement bottle and a relatively inexpensive end cap. Accordingly, the present cleaning system is not only easily implemented, but is also time saving and highly effective in removing organic debris from the internal channel of the endoscope.

While this invention has been explained with reference to the structure disclosed herein, it is not confined to the details set forth and this invention is intended to cover any modifications and changes as may come within the scope of the following claims:

What is claimed is:

1. Apparatus for cleaning the channels of an endoscope having an air channel, a water channel and a suction channel, all of which are open to the distal end of the endoscope insertion tube, a support unit having engagement means for receiving a removable water bottle, said removable water bottle having a water chamber connected to the water channel of the endoscope and an air chamber connected to the air channel of the endoscope, a first pump for delivering air into the air chamber of said removable water bottles a second suction pump connected to the suction channel and control means for selectively passing air and water through said air and water channels, said apparatus comprising:

an end cap removably fitted over the distal end of the endoscope insertion tube to provide a fluid tight seal therebetween, said end cap further including a reservoir for collecting fluids passed through the air and water channels, a replacement bottle for replacing said removable water bottle, said replacement bottle being receivable in said engagement means of said support unit, said replacement bottle further having a fluid chamber for containing a quantity of cleaning solution and an air chamber over said fluid chamber, said replacement bottle further including means to connect the fluid chamber to both the air channel and the water channel of the endoscope, whereby cleaning solution is passed through the air and water channels in the end cap reservoir and exhausted from the reservoir through the suction channel upon activation of at least said second suction pump.

2. The apparatus of claim 1 wherein said endoscope includes a biopsy port that is connected into said suction channel and further including a means for containing a cleaning solution connected in fluid tight closure with said biopsy port whereby said cleaning solution is drawn from said means through said port when the suction pump is activated.

3. The apparatus of claim 1 wherein said replacement bottle further includes a removable cap whereby the bottle can be refilled with a rinse solution once the cleaning solution is exhausted whereby the channels can be rinsed after they are cleaned.

4. The apparatus of claim 1 wherein said end cap is formed of an elastomeric material.

5. The apparatus of claim 1 wherein said replacement bottle has a shape that corresponds substantially to that of said removable water bottle.

6. A method of cleaning the channels of an endoscope containing an air channel, a water channel and a suction channel, all of which are open at the distal tip of the endoscope, a support unit having engagement means for receiving a removable water bottle, the removable water bottle having a water chamber that is connected to the water channel of the endoscope and an air chamber over the water chamber connected to an air channel of the endoscope, a first pump for delivering air into the air chamber of the removable water bottle, a second suction pump connected to the suction channel and control means for selectively passing air and water through said air and water channels, said method including the steps of placing an end cap over the distal end of the endoscope, said end cap having a fluid reservoir for receiving fluids discharged from said channels, replacing the removable water bottle with a replacement bottle filled with a cleaning solution, said replacement bottle being received in the engagement means of the support unit and having means for connecting a fluid chamber in said bottle to both the air channel and the water channel, and activating at least said second suction pump whereby cleaning solution is passed through the air and water channels into said end cap and drawn out of said end cap through said suction line.

7. The method of claim 6 wherein said endoscope includes a biopsy port passing into said suction channel and includes the further step of inserting a means filled with a cleaning solution into said biopsy port whereby said solution is automatically drawn from said means by said suction pump.

8. The method of claim 6 wherein the replacement bottle has a shape that corresponds substantially to that of the removable water bottle.

9. The method of claim 6 that further includes the step of refilling the cleaning bottle with a rinse solution after the cleaning solution is exhausted and passing the rinse solution through said channels.

10. The method of claim 9 that includes the further step of maintaining the pumps activated after the rinse solution is exhausted to pass air through said channels to promote drying of said channels.

11. The method of claim a that includes the further steps of collecting the cleaning and rinse solutions drawn through said suction line and disposing of said collected solutions.

\* \* \* \* \*